United States Patent [19]

Lindgren

[11] Patent Number: 4,802,483
[45] Date of Patent: Feb. 7, 1989

[54] HEART PACEMAKER FOR AVOIDING PACEMAKER MEDIATED TACHYCARDIA AT MODE SWITCHING

[75] Inventor: Anders Lindgren, Taeby, Sweden

[73] Assignee: Siemens Aktiengesellschaft, Berlin and Munich, Fed. Rep. of Germany

[21] Appl. No.: 22,006

[22] Filed: Mar. 5, 1987

[30] Foreign Application Priority Data

Mar. 18, 1986 [DE] Fed. Rep. of Germany ....... 3609072

[51] Int. Cl.$^4$ .................... A61N 1/00; H05G 00/00
[52] U.S. Cl. .............................................. 128/419 PG
[58] Field of Search ................... 128/419 PG, 419 PT

[56] References Cited

U.S. PATENT DOCUMENTS

| | | | |
|---|---|---|---|
| 4,202,341 | 5/1980 | Blaser | 128/419 PG |
| 4,344,437 | 8/1982 | Markowitz | 128/419 PG |
| 4,378,020 | 3/1983 | Nappholz et al. | 128/419 PG |
| 4,386,610 | 6/1983 | Leckrone | 128/419 PG |
| 4,407,287 | 10/1983 | Herpers | 128/419 PG |
| 4,412,541 | 11/1983 | Schaldach et al. | 128/419 PG |
| 4,421,114 | 12/1983 | Berkovits et al. | 128/419 PG |
| 4,421,116 | 12/1983 | Markowitz | 128/419 PG |
| 4,467,810 | 8/1984 | Vollmann | 128/419 PG |
| 4,485,818 | 12/1984 | Leckrone et al. | 128/419 PG |
| 4,515,161 | 5/1985 | Wittkampf et al. | 128/419 PG |
| 4,527,568 | 7/1985 | Rickards | 128/419 PG |
| 4,539,991 | 9/1985 | Boute et al. | 128/419 PG |
| 4,590,944 | 5/1986 | Mann et al. | 128/419 PG |

FOREIGN PATENT DOCUMENTS

| | | |
|---|---|---|
| 0076363 | 4/1983 | European Pat. Off. |
| 0147820 | 7/1985 | European Pat. Off. |

Primary Examiner—Francis J. Jaworski
Assistant Examiner—George Manuel
Attorney, Agent, or Firm—Hill, Van Santen, Steadman & Simpson

[57] ABSTRACT

An atrial synchronous heart pacemaker has circuitry for stimulating the atrium and sensing atrial events and circuitry for stimulating the ventricle and sensing ventricular events, switching circuitry connected to the atrial and ventricular stimulation circuitry which switches between selected stimulation modes, including an atrial synchronous mode, upon the occurrence of a predetermined heart condition, and a delay element connected to the switching circuitry which delays switching to the atrial synchronous mode until after a selected delay following sensing of the predetermined heart condition which caused the switching to the atrial synchronous mode. The pacemaker is particularly suited for improving transition between a VVI pacing mode and a DDD pacing mode.

20 Claims, 2 Drawing Sheets

Δt

HEART PACEMAKER FOR AVOIDING PACEMAKER MEDIATED TACHYCARDIA AT MODE SWITCHING

BACKGROUND OF THE INVENTION

1. Field of the Invention

The present invention relates to an atrial synchronous heart pacemaker, and in particular to a heart pacemaker switchable between a non-atrial synchronous and an atrial synchronous mode.

2. Description of the Prior Art

In heart pacemakers capable of switching between an atrial synchronous pacing mode and a non-atrial synchronous pacing mode, the generation of ventricular stimulation pulses in the atrial synchronous mode ensues after an AV delay time following the appearance of an atrium signal. Depending upon the selected smallest synchronous interval SSI, the ventricular stimulation frequency may vary within a relatively wide range from, for example, 50 through 150 impulses per minute. Such pacemakers generally contain a limit stage which determines the highest pulse rate. If an atrial signal occurs before a predetermined limit, which is derived from the difference between the smallest synchronous interval and the AV delay, the heart pacemaker switches to a non-atrial synchronous mode.

Although atrial synchronous heart pacemakers offer improved hemodynamics, it is known that a number of disadvantages exist in the use of such pacemakers. One such disadvantage is that a retrograde conduction in the heart may lead to a pacemaker-mediated tachycardia (PMT). In order to prevent PMT, it has been proposed to lengthen the refractory time in the atrium. Lengthening the refractory time, however, requires a reduction of the upper heartbeat frequency. Another proposal has been to extend the refractory time in the atrium only when the probability for a retrograde VA transition is high, such as, for example, following a premature ventricle contraction (PVC). As more recent investigations have shown, however, this approach can lead to a total inhibition of the heart pacemaker under certain circumstances, as reported in the periodical PACE, Vol. 8, November/December, 1985.

Whenever the heart pacemaker is to switch from the non-atrial synchronous mode e.g. VVI back to the atrial synchronous mode e.g. (DDD), the risk is particularly high that the synchronization will start precisely at an atrial activity triggered by retrograde transition, and thus will initiate a pacemaker-mediated tachycardia.

SUMMARY OF THE INVENTION

It is an object of the present invention to provide a heart pacemaker switchable between pacing modes, including an atrial synchronous mode, wherein the occurrence of pacemaker-mediated tachycardia in the transition to the atrial synchronous mode is prevented without disadvantageously influencing other pacing parameters, such as the highest possible heartbeat frequency.

The above object is achieved in accordance with the principles of the present invention in a heart pacemaker having a means for stimulating the atrium and sensing atrial events, a means for stimulating the ventricle and sensing ventricular events, switching means connected to the means for stimulating the atrium and the means for stimulating the ventricle for switching between selected stimulation modes, including an atrial synchronous mode upon the occurrence of a predetermined heart condition, and delay means connected to the switching means for delaying switching to the atrial synchronous mode until after a selected delay following sensing of the predetermined heart conditions which caused the switching to the atrial synchronous mode. Transition to the atrial synchronous mode is not undertaken until the second (or a later) atrial signal after the ventricular event, so that the first atrial signal does not yet trigger stimulation in the ventricle. The second atrial signal therefore cannot have been produced by retrograde transition of a ventricle signal, but rather is representative of a true atrium origin.

When such a true atrium origin does not occur, transition to the atrial synchronous mode is not undertaken after the first atrial signal until after a delay time $\Delta t$. In one embodiment of the invention, an AV-sequential stimulation of the heart can initially take place in order to depolarize the stimulation line system in an antegrade manner, thus to prevent the occurrence of pacemaker-mediated tachycardia. The delay time must be selected of such a size that the atrium has repolarized after the first atrial signal and, as a result, can be depolarized by the AV-sequential stimulation.

In a further embodiment of the invention the delay time is programmable. It has been determined that the delay time should be at least 200 ms.

In another embodiment of the pacemaker, a switching stage switches the heart pacemaker to a non-atrial synchronous mode when the atrial signal appears before a selected time limit. Switching back to the atrial synchronous mode is automatically undertaken when the atrium signal occurs again after the limit. Again, the switching back to the atrial synchronous mode occurs after the necessary delay, in order to avoid inducing tachycardia.

DESCRIPTION OF THE PREFERRED EMBODIMENTS

Figures 1A, 1B:
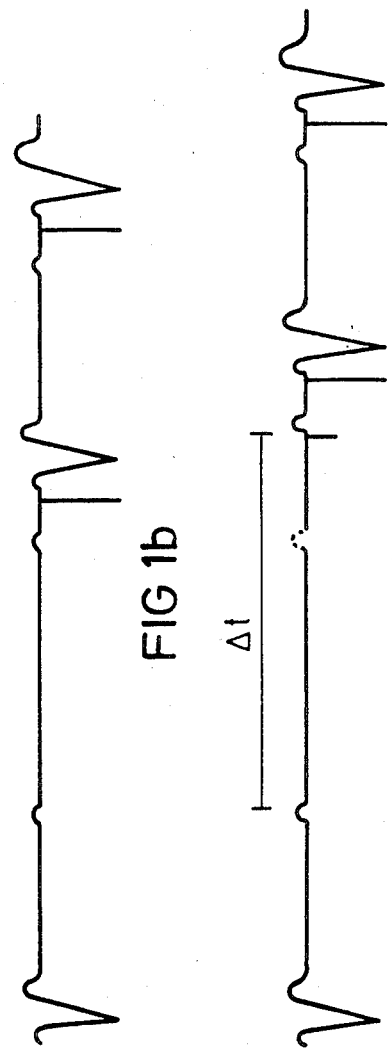
FIGS. 1a and 1b show EKG curves for explaining the operation of the heart pacemaker disclosed herein.

A first possible transition to the atrial synchronous mode in a heart pacemaker constructed in accordance with the principles of the present invention is schematically shown in FIG. 1a. After a QRS signal initiating the transition, the first P-wave does not trigger a synchronous ventricular stimulation pulse. For practical purposes, the first P-wave is suppressed. Atrial synchronous pacing does not begin until the occurrence of the second P-wave. The first P-wave may still have been caused by retrograde transition of the QRS signal, however this is not possible for the second P-wave. This insures that atrium-control will not begin until the occurrence of a true atrium origin event.

A second possible transition to the atrial synchronous mode in the heart pacemaker constructed in accordance with the principles of the present invention is shown in FIG. 1b. Transition is again initiated by a QRS signal. The first atrial signal following this QRS signal triggers a delay time $\Delta t$. The delay time must be selected of such a size that the atrial has repolarized after the first atrium signal. AV-sequential stimulation occurs at the end of the delay time Δt. The AV-sequential stimulation initially depolarizes the stimulation line system in an antegrade manner.

Figure 2:
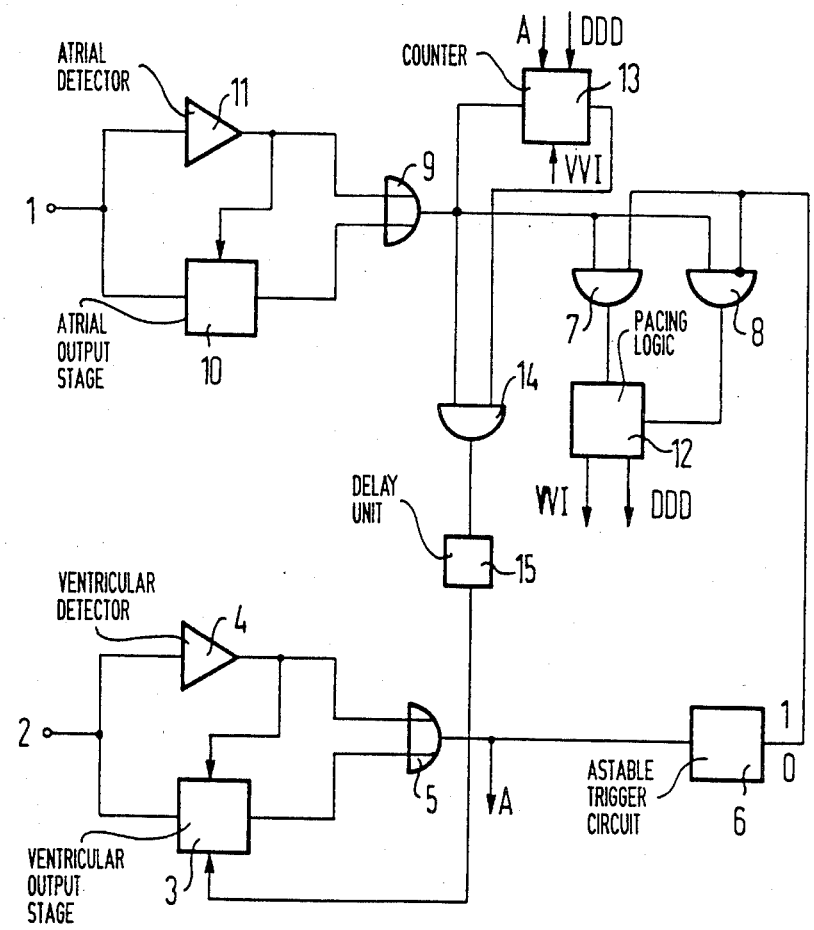
FIG. 2 is a block circuit diagram of a heart pacemaker constructed in accordance with the principles of the present invention.

As shown in the circuit diagram of FIG. 2, atrial signals are supplied to a terminal 1, and ventricular signals are supplied to a terminal 2. Pulses from a ventricular output stage 3 and a ventricular detector 4 are supplied through an OR gate 5 to switch an astable trigger circuit 6. The switching time of the astable trigger circuit 6 corresponds to the difference between the smallest synchronous interval and the selected AV delay time. A logic "1" is at the output of the trigger circuit 6 during the astable condition; a logic "0" is at the output otherwise. The output of the trigger circuit 6 is supplied to an AND gate 7 and is also supplied to the inverter input of another AND gate 8. The outputs of an atrial output stage 10 and an atrial detector 11, each connected to the terminal 1, are supplied to an OR gate 9, which has an output connected to respective inputs of the AND gates 7 and 8. The atrial detector 11 monitors atrial activity (P-waves).

If, following a ventricular event, an atrial event is detected in the time during which the output signal of the astable trigger circuit 6 is a logic "1" (i.e., when the sensed atrial activity exceeds the highest synchronous frequency of the pacemaker) a signal is supplied to pacing logic 12 from the AND gate 7, causing a pacing mode change from, for example, DDD mode to VVI mode. If an atrial event is not subsequently detected until the output signal of the trigger circuit 6 has returned to logic "0", the control logic 12 is supplied with an output signal from the AND gate 8, causing the pacemaker to return to the DDD mode.

The output signal of the OR gate 9 is also supplied to a P-wave counter 13, having an output signal which is forwarded to a further AND gate 14. The output of the OR gate 9 is supplied to the second input of the AND gate 14. The output of the AND gate 14 operates an AV delay element 15, whose output signal is supplied to the ventricular output stage 3. The P-wave counter 13 continues to receive a control signal A, corresponding to ventricular events, as well as the output signals from the control logic 12. For the VVI mode, the counter 13 is reset to 0. Upon the occurrence of a renewed DDD signal from the control logic 12, the counter 13 is enabled by the first signal A corresponding to a ventricular event. Given a counter reading of two or greater, a logic "1" is at the output of the counter 13. In this case, the output signals of the OR gate 9 are supplied through the AND gate 14 and the AV delay stage 15 to the ventricular output stage 3. The first atrial signal which occurs after switching to the DDD mode is thus suppressed because the counter 13 still has a logic "0" at its output given a count value of "1" and the AND gate 14 is thus inhibited.

Every time the mode control logic 12 switches the pacemaker from a VVI mode to a DDD mode, the circuit disclosed herein insures that this transition does not occur until at least the second atrial signal following the ventricular event which triggered the switching. It is also possible for the transition to be delayed until a later transition signal, by suitable programming of the counter 13.

The circuit disclosed herein has been shown for switching the heart pacemaker between VVI and DDD modes. It is within the inventive concept disclosed herein, however, to use the circuitry for controlling transition between other pacing modes which include an atrial-synchronous mode.

Although modifications and changes may be suggested by those skilled in the art it is the intention of the inventor to embody within the patent warranted hereon all changes and modifications as reasonably and properly come within the scope of his contribution to the art.

I claim as my invention:

1. A heart pacemaker comprising:
   means for stimulating the atrium and sensing atrial events;
   means for stimulating the ventricle and sensing ventricular events;
   switching means connected to said means for stimulating the atrium and to said means for stimulating the ventricle for switching between selected stimulation modes, including an atrial synchronous mode, upon the occurrence of a predetermined heart condition; and
   delay means connected to said switching means for delaying switching to said atrial synchronous mode until after a selected delay following sensing of the predetermined heart condition which caused the switching to said atrial synchronous mode.

2. A heart pacemaker as claimed in claim 1, wherein said delay means is a delay means for delaying switching to said atrial synchronous mode until the occurrence of a second or later atrial signal following a most recent ventricular signal.

3. A heart pacemaker as claimed in claim 2, further comprising a P-wave counter which begins counting with the occurrence of said most recent ventricular event and which retains a first counter output until a selected number of counts, said counter connected to said means for stimulating the ventricle for enabling stimulation of the ventricle after the occurrence of selected number of counts.

4. A heart pacemaker as claimed in claim 1, wherein said delay means includes a time delay element for determining said selected delay.

5. A heart pacemaker as claimed in claim 4, wherein said time delay element is programmable.

6. A heart pacemaker as claimed in claim 4, wherein said time delay element has a time delay of at least 200 ms.

7. A heart pacemaker as claimed in claim 4, further comprising means for initially operating said heart pacemaker in an AV-sequential stimulation mode for the first pulse following switching to said atrial synchronous mode.

8. A heart pacemaker comprising:
   means for stimulating the atrium and sensing atrial events;
   means for stimulating the ventricle and sensing ventricular events;
   switching means connected to said means for stimulating the atrium and said means for stimulating the ventricle for switching between an atrial synchronous stimulation mode and a non-atrial synchronous stimulation mode, said pacemaker normally operating in said atrial synchronous mode and said switching means switching to said non-atrial synchronous mode upon the occurrence of atrial events above a selected rate and switching back to said atrial synchronous mode when said atrial events fall below said selected rate; and
   delay means connected to said switching means for delaying switching to said atrial synchronous mode until a selected time after said atrial events fall below said selected rate.

9. A heart pacemaker as claimed in claim 8, wherein said delay means delays switching to said atrial synchronous mode until the occurrence of a second atrial event following a most recent ventricular event.

10. A heart pacemaekr comprising:
   means for stimulating the atrial an sensing atrial events;
   means for stimulating the ventricle and sensing ventricular events, said means having a control input;
   switching logic connected to said means for stimulating the atrium and to said means for stimulating the ventricle, said switching logic normally operating said pacemaker on an atrial synchronous mode and being switchable to operate said pacemaker in a non-atrial synchronous mode;
   control means for causing said switching logic to switch to said non-atrial synchronous mode if said atrial events occur faster than a selected rate and for causing said switching logic to switch back to said atrial synchronous mode when said atrial events occur below said selected rate; and
   a P-wave counter having an output connected to said control input of said means for stimulating the ventricle and having inputs respectively connected to said means for stimulating the atrium and to said switching logic, said counter counting the number of atrial events occurring after said switching logic is switched back to said atrial synchronous mode after being in said non-atrial synchronous mode, and preventing stimulation of said ventricle until a selected number of atrial events have been counted.

11. A heart pacemaker as claimed in claim 10, wherein said selected number of atrial events is two.

12. A heart pacemaker as claimed in claim 10, wherein said switching logic is switching logic normally operating said pacemaker in an atrial synchronous mode and being switchable to operate said pacemaker in a ventricle inhibited mode.

13. A heart pacemaker as claimed in claim 12, wherein said switching logic is switching logic normally operating said pacemaker in an atrial synchronous mode and being switchable to operate said pacemaker in a VVI mode.

14. A heart pacemaker as claimed in claim 10, wherein said switching logic is switching logic normally operating said pacemaker in a DDD mode and being switchable to operate said pacemaker in a non-atrial synchronous mode.

15. A heart pacemaker as claimed in claim 14, wherein said switching logic is switching logic normally operating said pacemaker in a DDD mode and being switchable to operate said pacemaker in a VVI mode.

16. A heart pacemaker as claimed in claim 10, wherein said selected number of atrial events is greater than two.

17. A heart pacemaker as claimed in claim 8, wherein said switching means is switching means for switching between an atrial synchronous stimulation mode and a ventricle inhibited stimulation mode.

18. A heart pacemaker as claimed in claim 17, wherein said switching means is switching means for switching between an atrial synchronous stimulation mode and a VVI stimulation mode.

19. A heart pacemaker as claimed in claim 8, wherein said switching means is switching means for switching between a DDD stimulation mode and a non-atrial synchronous stimulation mode.

20. A heart pacemaker as claimed in claim 19, wherein said switching means is switching means for switching between a DDD stimulation mode and a VVI switching mode.

* * * * *